(12) United States Patent
Seo et al.

(10) Patent No.: US 7,185,530 B2
(45) Date of Patent: Mar. 6, 2007

(54) DEVICE TO MEASURE THE SOLIDIFICATION PROPERTIES OF A LIQUID FILM AND METHOD THEREFOR

(75) Inventors: Kab Sik Seo, Kingsport, TN (US); Jessica Dee Posey-Dowty, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/024,912

(22) Filed: Dec. 20, 2004

(65) Prior Publication Data

US 2005/0132781 A1  Jun. 23, 2005

Related U.S. Application Data

(60) Provisional application No. 60/531,740, filed on Dec. 22, 2003.

(51) Int. Cl.
*G01N 11/10* (2006.01)
(52) U.S. Cl. ..................... 73/54.23; 73/54.28
(58) Field of Classification Search ............... 73/54.23
See application file for complete search history.

(56) References Cited

U.S. PATENT DOCUMENTS 4,539,838 A * 9/1985 Fraleigh .................... 73/54.23

| 4,799,453 A | | 1/1989 | Nobbs et al. |
| 5,303,578 A | * | 4/1994 | Williams et al. ........... 73/54.24 |
| 6,571,610 B1 | * | 6/2003 | Raffer ....................... 73/54.35 |
| 6,588,254 B1 | * | 7/2003 | Foster et al. ............... 73/54.23 |

OTHER PUBLICATIONS

J. Polymer Science, Part C, No. 35, pp. 3-21, 1971.
Macosko, "Rheology, Principles, Measurements and Applications", Chapter 5, VCH Publishers, Inc., 1994.
Strivens, "The Rheology of Paints" in "Paint and Surface Coatings—Theory and Practice", Chapter 15, Lambourne and Strivens Ed., 2nd Edition, William Andrew Publishing, 1999.

* cited by examiner

*Primary Examiner*—Hezron Williams
*Assistant Examiner*—Paul M. West
(74) *Attorney, Agent, or Firm*—Tammye L. Taylor; Bernard J. Graves, Jr.

(57) ABSTRACT

The present invention is directed to an apparatus and a method for monitoring the viscoelastic properties, of a liquid film (e.g. coating). The apparatus comprises a substrate supporting a liquid film, a probe to contact the liquid film, means for effecting relative movement between the probe and the substrate and means for monitoring the resistance to movement of the probe in contact with the film to obtain a measurement of the solidification properties of the liquid film. This apparatus and method are particularly useful in comparing the effects of film formers, viscosity modifiers, solvents, and minerals on the drying rate of coatings at the early stage of film formation.

17 Claims, 9 Drawing Sheets

Side view

Top view

DEVICE TO MEASURE THE SOLIDIFICATION PROPERTIES OF A LIQUID FILM AND METHOD THEREFOR

This application claims the benefit of U.S. Provisional Application Ser. No. 60/531,740, filed Dec. 22, 2003, and is hereby incorporated by reference.

BACKGROUND

The present invention is directed to an apparatus and a method for monitoring the solidification properties, including the viscoelastic properties, of a solidifiable liquid film (e.g. coating).

The performance of a liquid film, specifically a coating, depends on many variables, such as its viscosity, its elasticity, its surface tension and the rate of solvent evaporation. These variables must be optimized to achieve desirable characteristics, such as flow and leveling, anti-sag, anti-mounding, drying rate, pigment dispersion and other preferred characteristics. For example, after a liquid film is deposited to a substrate, the liquid film needs time to level. However, the liquid film must also dry quickly so as not to sag. Good flow and leveling characteristics often require low viscosity liquid films with Newtonian behavior while good anti-sag requires liquid films having high viscosity at low shear rates. The challenge when forming films is to control these competing properties to provide liquid films with the desired characteristics.

The dryness of a liquid film on a substrate is often described as a surface phenomenon and is defined in many different ways, such as by viscosity. For example, the American Society for Testing and Materials (ASTM) describes the standard test method for measuring times of drying or curing of organic coatings using mechanical recorders in ASTM D5895-01. In this test a coating is applied to a glass strip and a stylus placed on the wet coating and moved either in a linear motion or in a 360° arc at a constant speed. Various drying times, e.g., set-to-touch time, and tack-free time, dry-hard time, and dry-through time, are visually determined by observing the track of the stylus on the glass slide. Unfortunately test results of this kind are quite subjective and difficult to accurately reproduce.

Many other ways have been proposed to measure the dryness or the drying rate of a liquid film. For example, the dry-to-touch time is commonly used and is defined by the time from the application of a liquid film onto a surface to the time the film can be touched with an object (usually the hand of the tester) without the film being transferred from the surface to the object (hand). However, the dry-to-touch time is dependant upon many subjective criteria, such as how much pressure is applied, and is not consistently reproducible.

Another method to determine the drying rate is scratching a coating that has been applied to a surface using a pencil or other sharp object (e.g. Tukon test) at certain elapsed times. Yet another method for measuring the relative drying rate is a gravimetric method that measures the amount of solvent loss from the liquid film.

A drawback to the methods mentioned above is that they only measure properties related to the viscosity of the liquid film. In addition to the viscosity, solidifiable liquid films also exhibit elasticity that changes during the solidification process. A direct measurement of the viscoelastic properties (the viscosity and elastic properties of a liquid film) provides more accurate and detailed information of the solidification process of a liquid film.

A frequently used technique to monitor the viscoelatic properties of a coating deposited on a substrate is the torsion braid analysis (J. Polymer Sci. Part C, No. 35, pp 3–21 (1971)). The torsion braid analysis monitors decaying amplitude and frequency to determine the affect of a liquid film as it solidifies on a substrate. One problem with this analysis is that the restoring force or the elastic modulus of the substrate is so much stronger than that of the liquid film that it is very difficult to determine the relatively small effect of the liquid film on the total torque. In addition, this test is sensitive to such variables as non-uniform distribution of the coating on the substrate and irregular drying patterns, which reduce the accuracy and reproducibility of the test.

German patent DE 19806905 provides another technique for measuring changes in the viscoelastic properties of a liquid film as it solidifies on a thin hard plate. The technique disclosed in DE 19806905 measures the viscoelastic properties by measuring the resonance frequency applied either in a torsional or flexural mode using a substrate, such as a rectangular plate, coated with a liquid film. The resultant force and the resonance frequency shift that occur as the liquid film dries are measured by a piezoelectric material and converted into loss (G") and storage (G') moduli.

U.S. Pat. No. 4,799,453 and Japanese patent 63145943 describe apparatus that monitor film formation during curing by UV, oxidation, and evaporation of solvents. In these patents the solidification characteristics of the liquid film are electronically monitored by measuring the resistance to movement of a stylus through the liquid film as it solidifies. Although this technique improves the accuracy as compared to other techniques, such as the swab resistance test or testing the film surface with one's thumb, it monitors changes only in the hardness of the film as it dries.

German patent DE 3420341 teaches a technique to measure the drying time of a liquid film by a rotating an object, such as a ball, on an inclined disc. The position of the ball placed eccentrically on a coated disc is monitored by a light detector. The inclined disc is rotated by a motor to keep the ball at the same position on the disc. The rotational speed of the disc necessary to maintain the ball in a stationary position is proportional to the viscosity of the liquid film. The viscosity is plotted as a function of time to provide a viscosity verses time measurement for the liquid film. In addition to requiring intricate and expensive equipment, this method only measures the viscosity or stickiness of the liquid film and does not measure other solidification properties, such as elasticity of the liquid film.

In view of the above, it is apparent that there is a need for a means of reliably, consistently and accurately measuring the solidification properties of a liquid film on a substrate under laboratory conditions.

SUMMARY OF THE INVENTION

The present invention provides an apparatus for reliably, consistently and accurately monitoring the solidification properties of a solidifiable liquid film. The present invention provides an accurate monitoring by minimizing the intrusion on the liquid film, thus mimicking the actual solidification process of a liquid film. By measuring the change in the viscosity and the elasticity with an apparatus, the present invention provides a consistently objective and reproducible method for monitoring the solidification properties of a liquid film.

The article of the present invention comprises a substrate, such as a trough or plate, a probe mounted so as to contact a liquid film on the substrate, a means of effecting relative movement of the probe and the substrate so that the probe moves with respect to the substrate and contacts the film while the film is solidifying, and a means for monitoring the resistance to movement of the probe contacting the film to obtain a measurement of the solidification properties of the film.

In another embodiment, the present invention is a process for measuring the viscoelastics properties of a liquid film on a substrate comprising the steps of contacting a probe with the liquid film, moving the probe relative to the substrate so that the probe moves with respect to the surface of the substrate and in contact with the film while the film is solidifying, and monitoring the change in the solidification properties of the film.

DETAILED DESCRIPTION OF THE INVENTION

Figure 1:
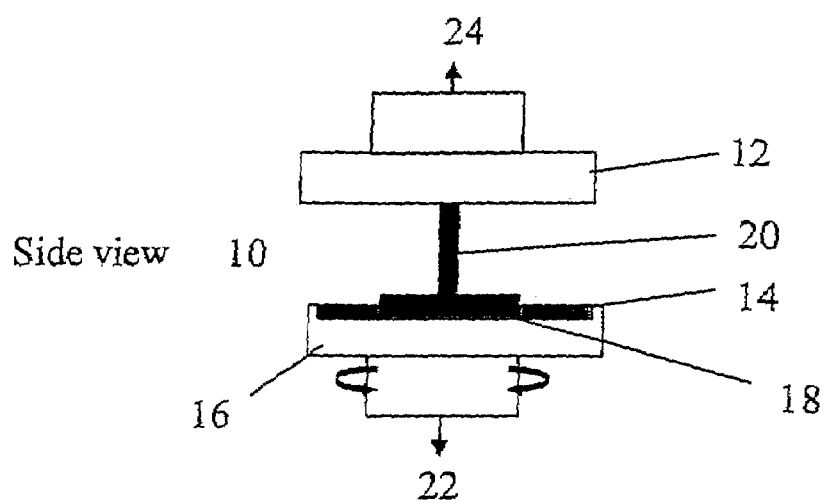
FIG. 1 is a side view of a preferred embodiment of an apparatus of the present invention.

The present invention may be understood more readily by reference to the following detailed description of the invention, including the appended figures referred to herein, and the examples provided therein. It is to be understood that this invention is not limited to the specific apparatus and processes described, as specific apparatus and processes and/or process conditions for measuring the viscoelastic properties and the solidification properties of liquids may, of course, vary depending on variable, such as the type of liquid being measured and the equipment available.

It must also be noted that, as used in the specification and the appended claims, the singular forms "a," "an" and "the" include plural referents unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

By "comprising" or "containing" is meant that at least the named apparatus, element, or method step etc. must be present in the article or method, but does not exclude the presence of other materials, article, elements, or method steps, etc, even if the other such materials, articles, elements, or method steps etc. have the same function as what is named.

It is also to be understood that the mention of one or more method steps does not preclude the presence of additional method steps or intervening method steps between those steps expressly identified.

Viscosity refers to the resistance of a liquid to flow.

Elasticity refers to the ability of a material, such as a liquid, to store part of the applied energy to it. The material may recover part of its deformation when the stress is removed (elastic recoil as in the case of rubber band).

Viscoelasticity refers to both viscosity and elasticity being exhibited by a material, such as by a solidifiable liquid.

The viscosity and elasticity values for the liquid films are expressed in relative terms as a function of the change over time in these values.

Flow and leveling refer to the property of a liquid film, such as a coating, that determines how easily and uniformly the liquid spreads out after it is applied on a substrate.

Sag resistance refers to the resistance of a solidifiable liquid film to dripping or downward flow due to gravity.

Mound or mounding refers to bumps that form as a solidifiable liquid film solidifies on a substrate.

Pigment wetting refers to the wetting of pigments by a liquid to uniformly disperse the pigments in a liquid film.

Rheometer is an instrument that may be used to measure rheological properties (viscosity, elasticity, normal force and others) of liquids. A rheometer may have a means of moving a probe relative to a substrate, such as a motor, and a means of detecting resistance, such as a sensor, also herein referred to as a transducer.

Dynamic oscillatory capability refers to the capability that a rheometer has to shear (or deform) a liquid film in an oscillatory fashion, which is a dynamic motion.

Discussion

One embodiment of the present invention includes the discovery of a method to monitor changes in the viscoelatic properties of liquid films, specifically solidifiable liquid films such as coatings, with minimum disturbance of the liquid during solidification. Another embodiment of the present invention is directed to an apparatus for monitoring the viscoelastic properties properties of a liquid film. The apparatus comprises a substrate, such as a trough or plate, preferably a flat plate, and a probe, such as a thin hard wire T-bar, preferably mounted on any conventional rheometer having dynamic oscillatory capability. The probe detects the resistance of the liquid film over time to provide the resistance to a sensing means that will measure the torque and the phase angle between the sinusoidal input signal from the sensor and the output signal from the probe as the liquid film solidifies. The torque and the phase angle are used to determine the complex viscosity (Eta*), viscous modulus (G") and the elastic modulus (G'). In a preferred embodiment, the probe is contacted with the liquid film as soon after the liquid film is introduced into the trough and remains in contact with the liquid film until the film becomes a solid.

The invention is suitable for determining the viscoelastic properties and the solidifying properties of a large variety of different types of liquid films, including soldifying including both convertible (the film capable of being re-dissolvable) and non-convertible films. Thus, for example, it is suitable for monitoring films which solidify as a consequence of being subjected to ultraviolet or infrared radiation or an electron beam, oxidation (e.g. films based on alkyd resins), heating (e.g. phenolic resins films), chemical reaction between reactive groups (e.g. epoxy resin based films), free radical formation (e.g. films which solidify after peroxide initiation), evaporation (i.e. films formed by removal of a liquid phase from a solution or emulsion), precipitation i.e. films of, for example, ink formed by changing the solvent balance of a solution so as to precipitate out a solid phase, etc. In a preferred embodiment the present invention is useful for films cured by oxidation and evaporation. Thus, the invention has many applications such as, for example, monitoring the drying of inks during printing, the curing of ultraviolet (U/V) curable (slow and fast) optical fiber coatings and the hardening of adhesives and paints. Also, the invention enables the influence of the substrate on the solidification properties of the film to be assessed.

The film thickness may be varied by the depth of the trough. Depending on the application, the trough may be any suitable size, shape or configuration that allows for a probe to measure the solidification properties of a liquid film. The trough preferably provides a laboratory reproduction of an actual liquid film solidification process. For example, if a paint is the liquid film to be monitored, then the trough is preferably shallow having a depth ranging from about 0.005 to about 5 mm, preferably from about 0.01 to about 1 mm, more preferably from about 0.05 to 0.3 mm and most preferably from about 0.1 to about 0.2 mm. The width should be wide enough to avoid any adverse effects from premature drying from the edges which may occur. In one embodiment, the width or the diameter (depending on whether the trough is square, rectangular, circular or other shape) of the trough ranges from about 2 mm to about 50 mm, preferably about 5 mm to about 30 mm, and more preferably from about 15 mm to about 25 mm. While these dimensions are provided for paints and other liquid films that are used as commercial coatings, it is within the scope of the present invention to modify the trough dimensions so that the liquid film or coating being tested mimics a liquid film or coating as it is typically used.

The probe may be any mechanical device that is capable of contacting the liquid film and detecting the change in resistance as the probe is moved in the liquid film as the film solidifies. Preferably, the probe has sufficient surface area contacting the liquid film, so that it can detect the resistance, but be small enough so that the probe does not interfere with the solidification of the liquid film. It is also within the scope of the present invention to reinforce the cross-bar (horizontal bar) of the T-bar structure. For example, a preferred embodiment of the probe is a T-bar, as shown in FIG. 1 (T-bar 20). Other examples of suitable probes may be any rod, paddle, knife edge, or the like, that can be contacted or submerged into the liquid film. For paint applications, a preferred T-bar has a diameter in the range from about 0.01 mm to about 2 mm, preferably from about 0.025 mm to about 0.3 mm and more preferably from about 0.05 to about 0.1 mm. The length of the T-bar ranges from about 2 mm to about 50 mm, preferably about 5 to about 20 mm, and more preferably from about 10- to about 15 mm. The cross-section of T-bar wire can vary and is not limited to a circular cross-section. The T-bar should have enough rigidity not to be effected by the dynamic properties of the liquid film, such as high carbon steel, stainless steel, tungsten carbide and the like. While these dimensions are provided for the present invention, specifically the use of a rheometer and the monitoring of solidification properties of paints and other coatings, it is within the scope of the present invention to modify the probe dimensions to suit the liquid film to be tested.

The solidification of a liquid film is sensitive to the thickness of the liquid film. In a preferred embodiment the thickness of the film is uniform in the portion of the film being measured. Therefore, precise control of the liquid film thickness is preferred. The film thickness may be varied by the depth of the trough. In a preferred embodiment the film is deposited, such as by pouring, injecting or pipeting, into the trough and the top surface of the trough is leveled to provide a consistent film thickness. The liquid film may be leveled by any means, such as by drawing a flat edge (e.g., glass slide edge) across the top of the trough to smooth and substantially level surface of the liquid film or injecting a precise amount of liquid to spread out by itself. A probe is then contacted with the liquid film. In a preferred embodiment one end of the probe is submerged into the liquid film to a point just above the bottom of the trough. The probe should not contact the bottom of the trough. The gap between the bottom of the trough (substrate) and the bottom portion of the probe will depend on variables such as, the type and size of the probe and the depth of the liquid film being monitored and shape of the trough. The typical gap between the bottom of the trough (the substrate) and the bottom part of the probe (shown in FIG. 1 as a T-bar 20) is in the range of about 0.01 to about 0.1 mm depending on the thickness of the probe (T-bar 20), size and depth of the trough and the liquid film thickness.

The solidification rate of a liquid film may be sensitive to the liquid film thickness, humidity, temperature and air flow rate. Therefore, in a preferred embodiment a controlled environmental chamber is desirable to provide constant humidity, temperature and gas flow rate to the liquid film.

The probe may be mounted on any suitable means. In a preferred embodiment, the probe is mounted on a rheometer that also comprises a means of either moving the probe relative to the substrate or moving the substrate relative to the probe and a monitoring means, such as a transducer. The probe may be moved in any manner that will provide resistance that can be measured. In a preferred embodiment the probe is moved in an oscillating manner relative to the substrate to measure the resistance of the liquid film and the phase angle between input and output signals as the film dries. Any means may be used to accomplish this movement, such as a motor or other mechanical means. The resistance detected by the probe can be measured by any suitable means including a transducer or other electronic sensor. From the resistance and the phase angle, the relative viscosity and elasticity of the liquid film can be determined and plotted over the time the film solidifies.

Referring now to FIG. 1, the solidification properties of a solidifiable liquid may be measured using apparatus 10 which comprises a T-bar mount 12 and a transducer 24 which measures the rheological properties of the liquid film 14. The liquid film 14, is supported by substrate 16 having a trough 18. The shape and dimensions of the trough 18 can vary and are not limited to a circular shape. A T-bar 20, functioning as a probe, is mounted to the rheometer and is partially submerged in the liquid film 14. The T-bar may penetrate the liquid film 14, so long as the T-bar does not contact the substrate 16. A motor 22 provides movement between the T-bar 20 and the substrate 16 and a transducer 24 measures the resistance to the movement of the probe to the liquid film as the film solidifies. The position of the probe 20 in the liquid film may be adjusted by changing the position of the transducer 24 head to which the probe is connected.

Figure 2:
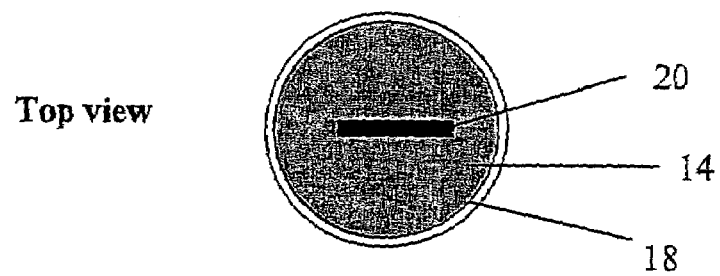
FIG. 2 is a top view of a preferred embodiment of a probe and a trough.

FIG. 2 provides a top view of the T-bar 20 contacting the liquid film 14 in trough 18. The means for effective relative movement between the probe and the substrate is preferably in an oscillating manner with minimal disturbance to the liquid film as it solidifies. In a preferred embodiment, the trough has sufficient distance between the T-bar and the edges of the trough so that any premature drying that may occur at the edges does not touch the oscillating T-bar.

This invention can be further illustrated by the following examples of preferred embodiments thereof, although it will be understood that these examples are included merely for purposes of illustration and are not intended to limit the scope of the invention unless otherwise specifically indicated.

EXAMPLES

In the following examples, the drying rate was measured either with the nitrogen gas flow over the coated plate in a closed chamber or in open air at ambient temperature between 24–26° C.

Example 1

Figure 3:
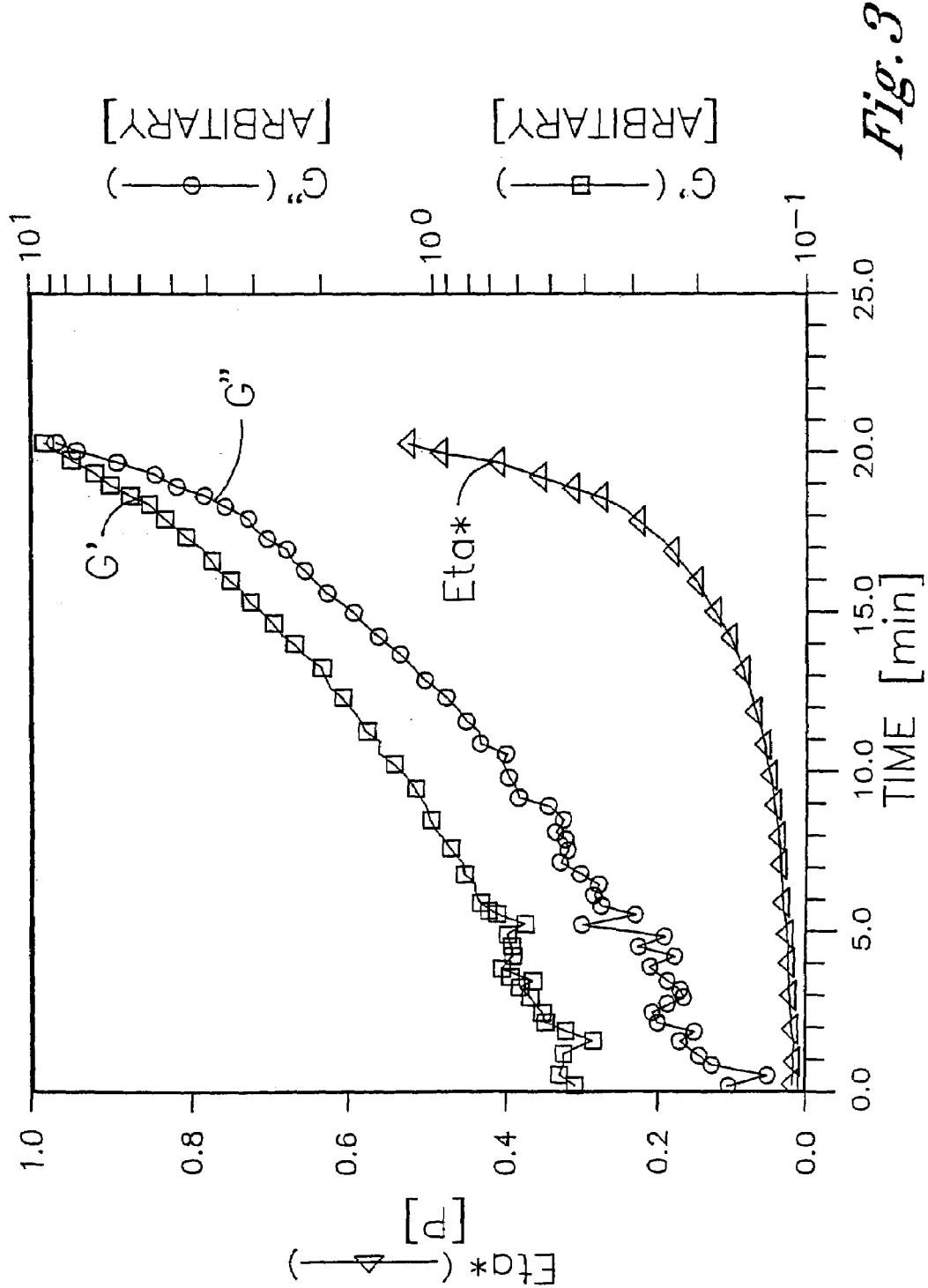
FIG. 3 provides a graphic representation of the viscoelastic properties verses time of a liquid carboxymethyl cellulose acetate butyrate (CMCAB ester) basecoat film in a 0.1 mm trough as more fully described in Example 1.

A 0.1 mm deep and 23 mm diameter circular trough was filled with approximately 0.1 ml of a coating formulation (a metallic basecoat containing carboxymethyl cellulose acetate butyrate, a cellulose ester available from Eastman Chemical Company in Kingsport, Tenn., under the tradename CMCAB) using a syringe. The trough was immediately scrapped to form a uniform surface by using the edge of a glass slide, and the T-bar probe (0.28 mm×15 mm, diameter×length) lowered to 0.05 mm gap and then the dynamic mechanical analyzer (ARES® available from TA Instruments in New Castle, Del.) was run at 100% strain and 25 rad/sec frequency. Changes in viscoelastic properties; Eta* (complex viscosity), G' (elastic modulus) and G" (viscous modulus) with time are illustrated in FIG. 3. The torque on the probe is small, especially during the early stage of the drying. To detect such a low torque, a high sensitivity transducer (e.g. 100 FRT on ARES from TA Instruments) should be used. The test should be stopped before the viscosity becomes too high to avoid damaging the probe Example 2

Figure 4:
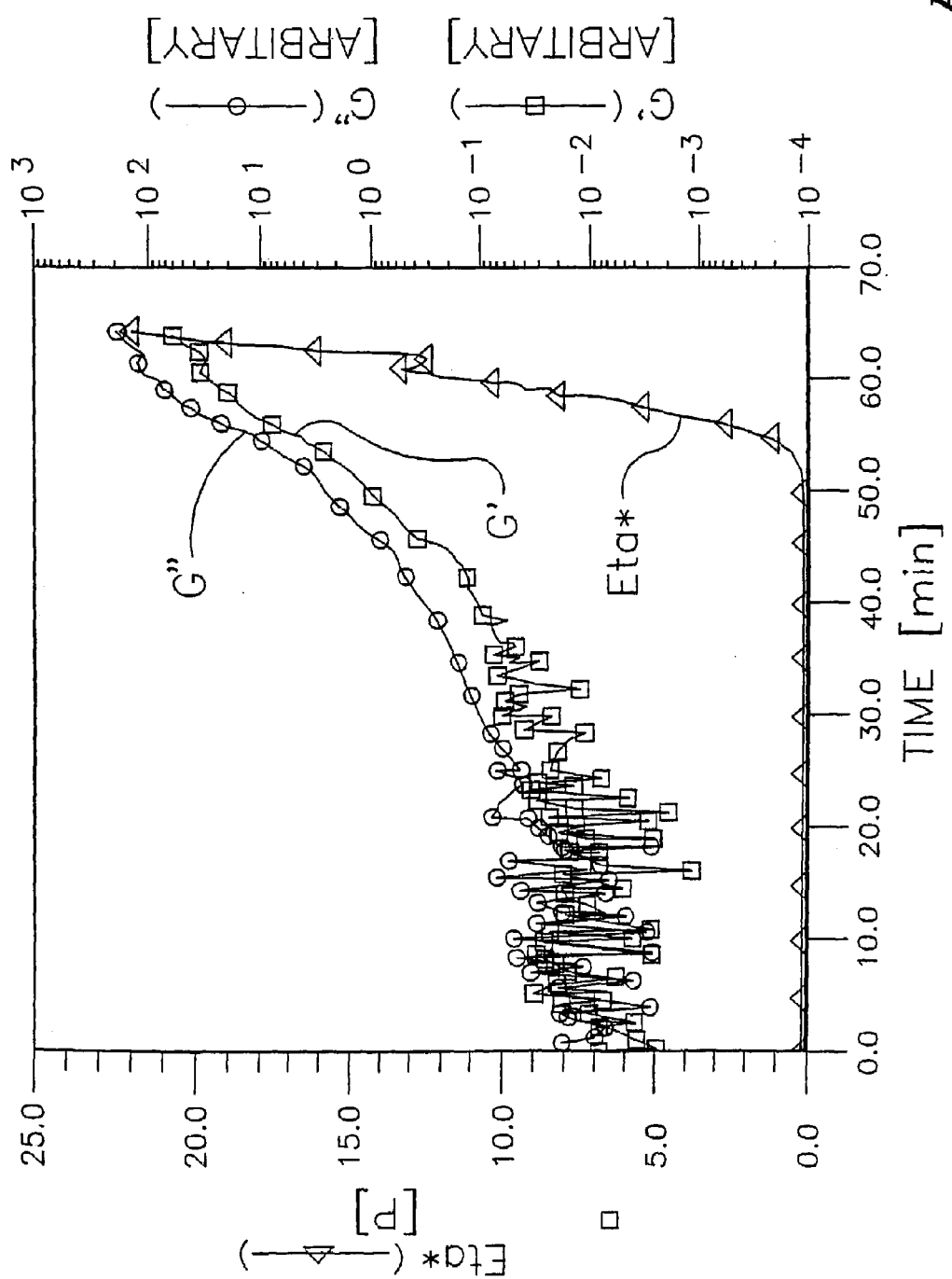
FIG. 4 provides a graphic representation of the viscoelastic properties verses time of a liquid acrylic latex dispersion film in a 0.2 mm trough as more fully described in Example 2.

A 0.2 mm deep and 23 mm diameter circular trough was injected with 0.1 ml of an acrylic latex dispersion using a syringe. The solution was spread evenly within the trough by using the edge of a glass slide or a stainless steel spatula. The T-bar probe (0.28 mm×15 mm, diameter×length) was lowered to 0.05 mm gap and the oven door which closes the trough and the T-bar was closed. The dynamic mechanical analyzer (ARES® from TA Instrument) was then started without purge gas. The dynamic test was conducted with 100% strain and 25 rad/sec frequency at ambient temperature. The complex viscosity and the moduli (elastic and viscous) are plotted in FIG. 4.

Example 3

Figure 5:
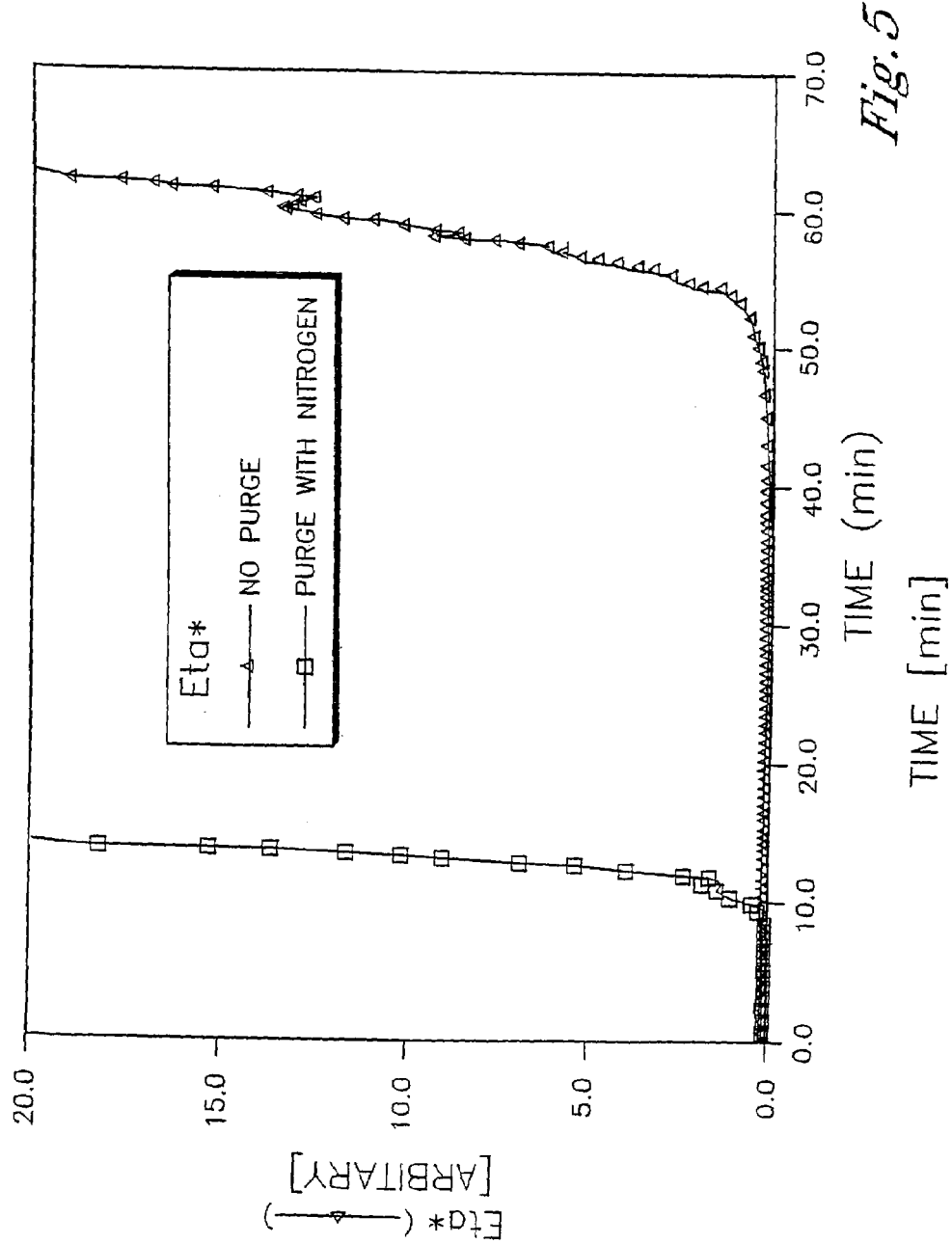
FIG. 5 provides a graphic representation of the viscoelastic properties (complex viscosity, Eta*) verses time of the liquid acrylic latex dispersion film in a 0.2 mm trough as described in Example 2, with and without nitrogen flow. This is more fully described in Example 3.

The same test described in Example 2 was conducted with a nitrogen purge with 4 standard cubic feet per hour flow rate in the closed oven. The complex viscosity is plotted together with the result from example 2 in FIG. 5.

Example 4

Figure 6:
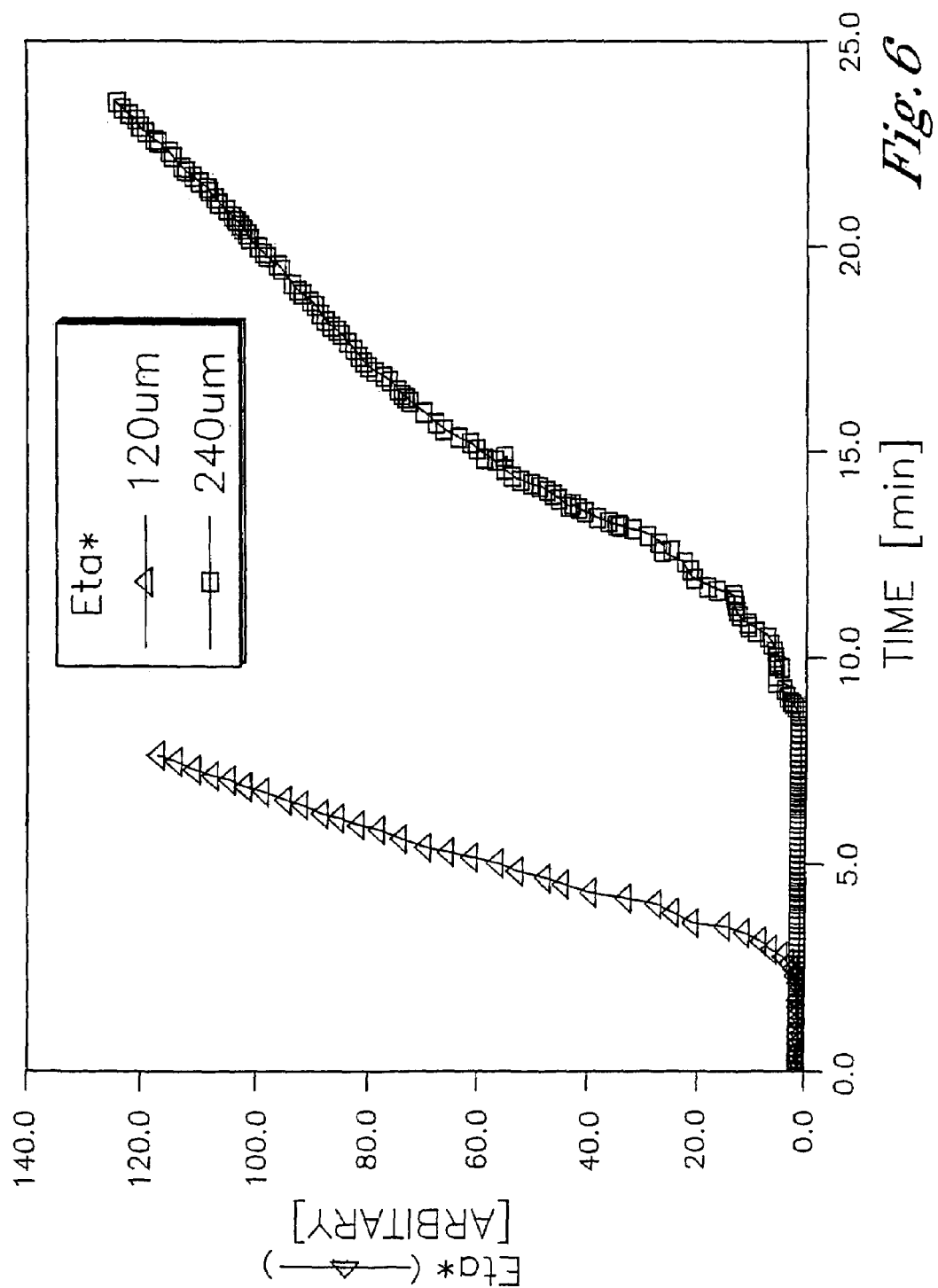
FIG. 6 provides a graphic representation of the viscoelastic properties (complex viscosity, Eta*) verses time of a lacquer solution film in a 0.1 mm trough and in a 0.2 mm trough as more fully described in Example 4.

A 0.1 mm deep and 23 mm diameter circular trough was filled with 0.05 ml of a clear CAB lacquer solution having the following formulation: cellulose acetate butyrate a base coat available from Eastman Chemical Company, Kingsport, Tenn. under the tradename CAB 381-0.5 in 10 weight percent, acrylic resin available from Rohm and Haas, Philadelphia, Pa., under the tradename Parloid B-66 in 7.7 weight percent, a plasticizer available from Solutia, Inc. in Saint Louis, Mo., under the tradename Santicizer 160 (Plasticizer) in 2 weight percent, methyl ethyl ketone 7.5 weight percent, n-butyl alcohol 11 weight percent, toluene 16 weight percent, methyl amyl ketone (MAK) in 9 weight percent, Tecsol C available from Eastman Chemical Company in 12.5 weight percent, and n-butyl acetate 23.5 weight percent. The solution was evenly spread by using the edge of a glass slide, which results in a layer approximately 120 μm thick. The T-bar probe (0.28 mm×15 mm, diameter×length) was lowered to 0.05 mm gap, and then the dynamic mechanical analyzer (ARES® from TA Instrument) started at 100% strain and 25 rad/sec frequency. The same sample was tested on a 0.2 mm deep trough with 0.1 ml of solution which was equivalent to a wet film approximately 240 μm thick. The results are plotted in FIG. 6.

Example 5

Figure 7:
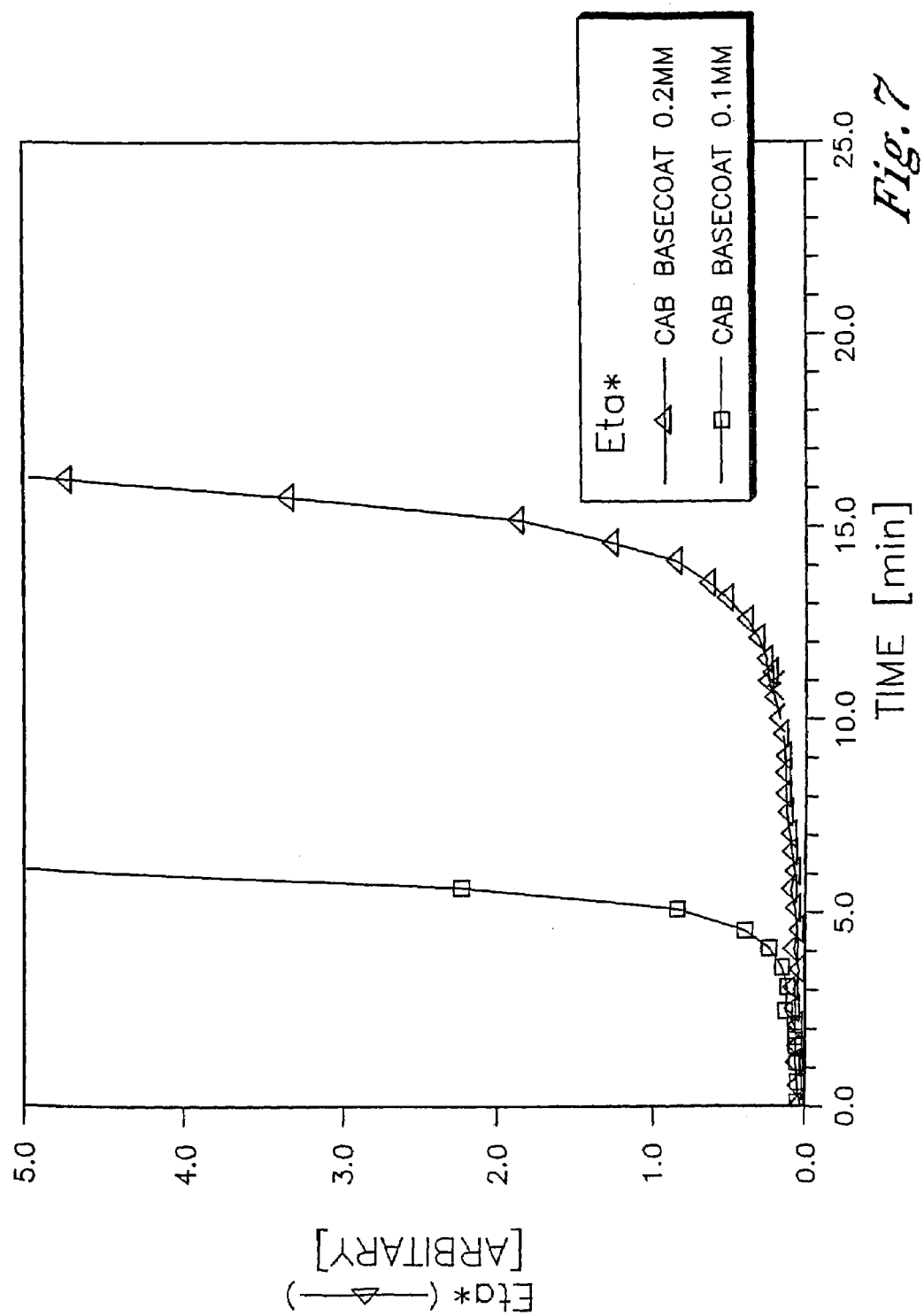
FIG. 7 provides a graphic representation of the viscoelastic properties (complex viscosity, Eta*) verses time of a CAB basecoat in a 0.1 mm trough and in a 0.2 mm trough as more fully described in Example 5.
Figure 8:
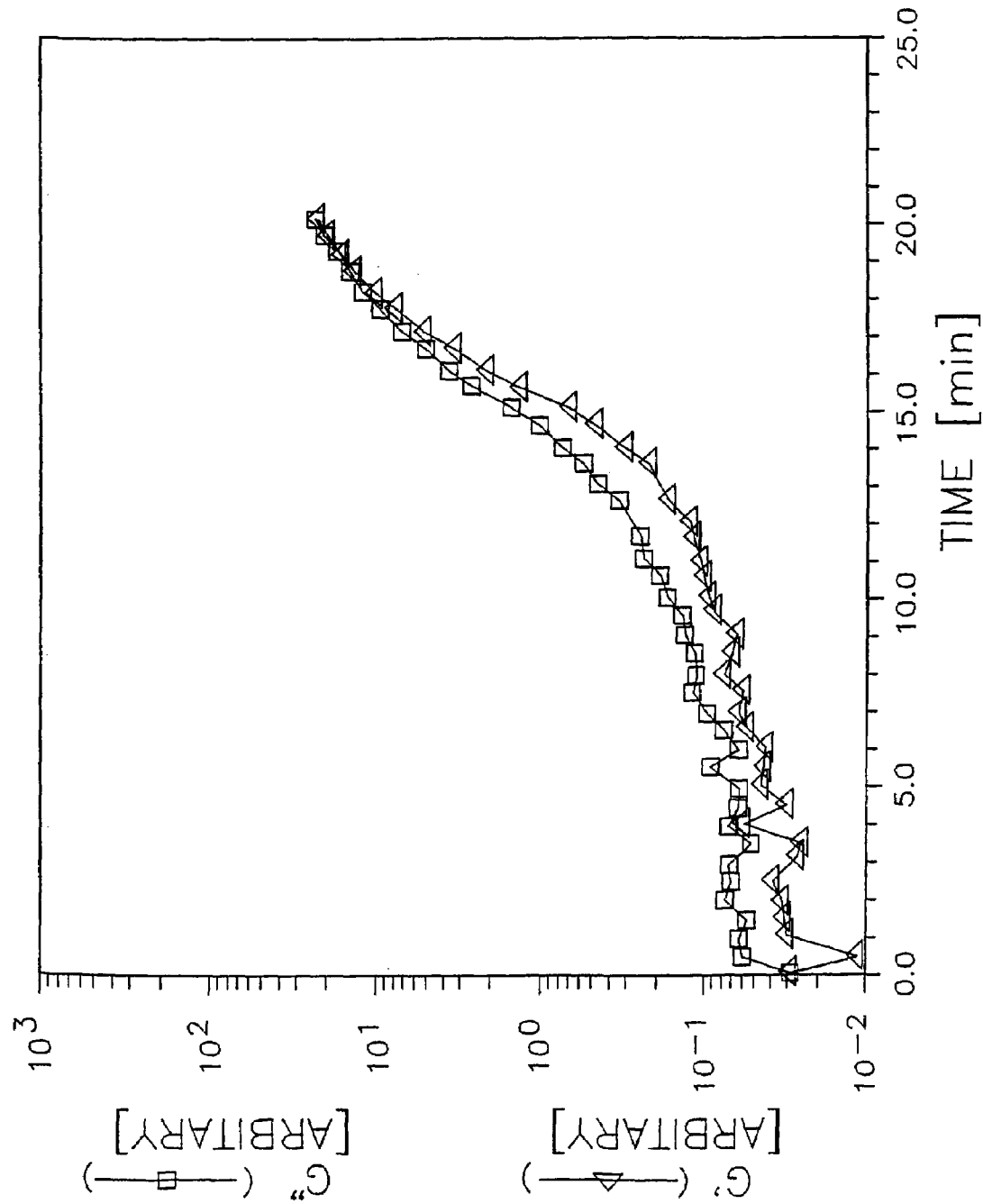
FIG. 8 provides a graphic representation of the viscoelastic properties (viscous (G") and elastic (G') moduli) verses time of a CAB basecoat in a 0.2 mm trough as more fully described in Example 5.
Figure 9:
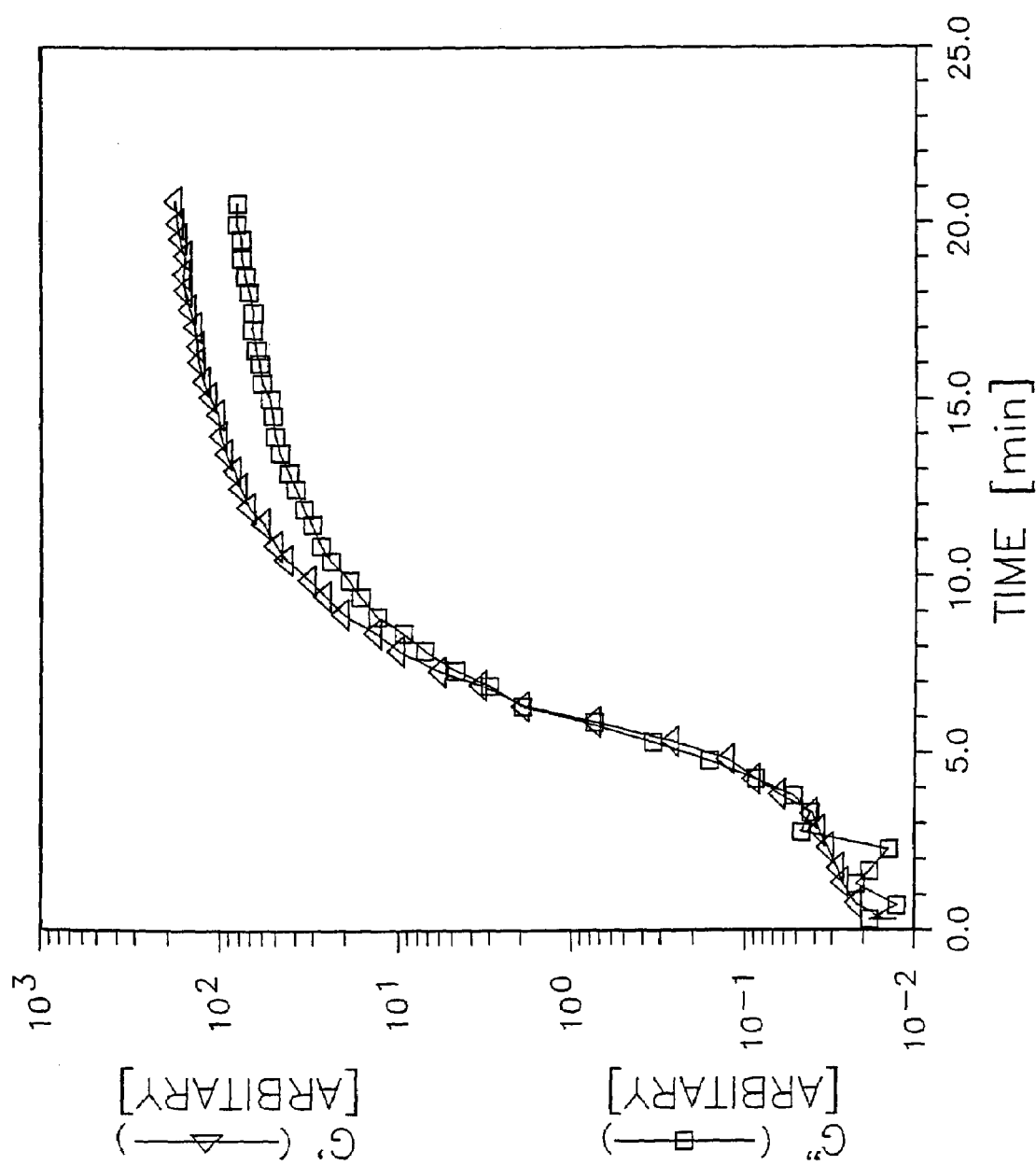
FIG. 9 provides a graphic representation of the viscoelastic properties (viscous (G") and elastic (G') moduli) verses time of a CAB basecoat in a 0.1 mm trough as more fully described in Example 5.

A 0.2 mm deep and 23 mm diameter circular trough was filled with 0.1 ml of a metallic basecoat based on cellulose acetate butyrate (CAB 381-2 from Eastman Chemical Company) having the following formulation: CAB 381-2 5.33 weight percent, polyester resin (Duramac 5776 from Eastman Chemical Company) 6.79, polyester resin with thixotropic properties (Duroftal PE9125SCA/50SNAX from UCB Company) 2.72 weight percent, melamine (Resimine HF480 from UCB company) 0.36 weight percent, wax dispersion (VP715A from Lubra Print) 0.57 weight percent, aluminum flake 3.23 weight percent and solvent 81%. The solvent is composed of n-butyl acetate contained in CAB 381-2 solution, n-butyl propionate contained in the metallic flake solution, PMA (propylene glycol monomethyl ether acetate) contained in Duramac 5776 and unknown solvent contained in Duroftal PE9125SCA/50SNAX. The metallic basecoat was evenly spread by using the edge of a glass slide. The T-bar probe (0.28 mm×15 mm, diameter×length) is lowered to 0.05 mm above the bottom of the substrate, the oven door was closed and then the dynamic mechanical analyzer (ARES® from TA Instrument) was run at 100% strain and 1 rad/sec frequency. The test was conducted with a nitrogen purge with 4 standard cubic feet per hour flow rate in the closed oven. The same sample was tested on a 0.1 mm deep trough. The viscosity changes as a function of drying time are plotted in FIG. 7, and the corresponding changes in elastic modulus (G') and viscous modulus (G") are plotted in FIG. 8 for 0.2 mm trough and FIG. 9 for 0.1 mm trough.

Example 6

Figure 10:
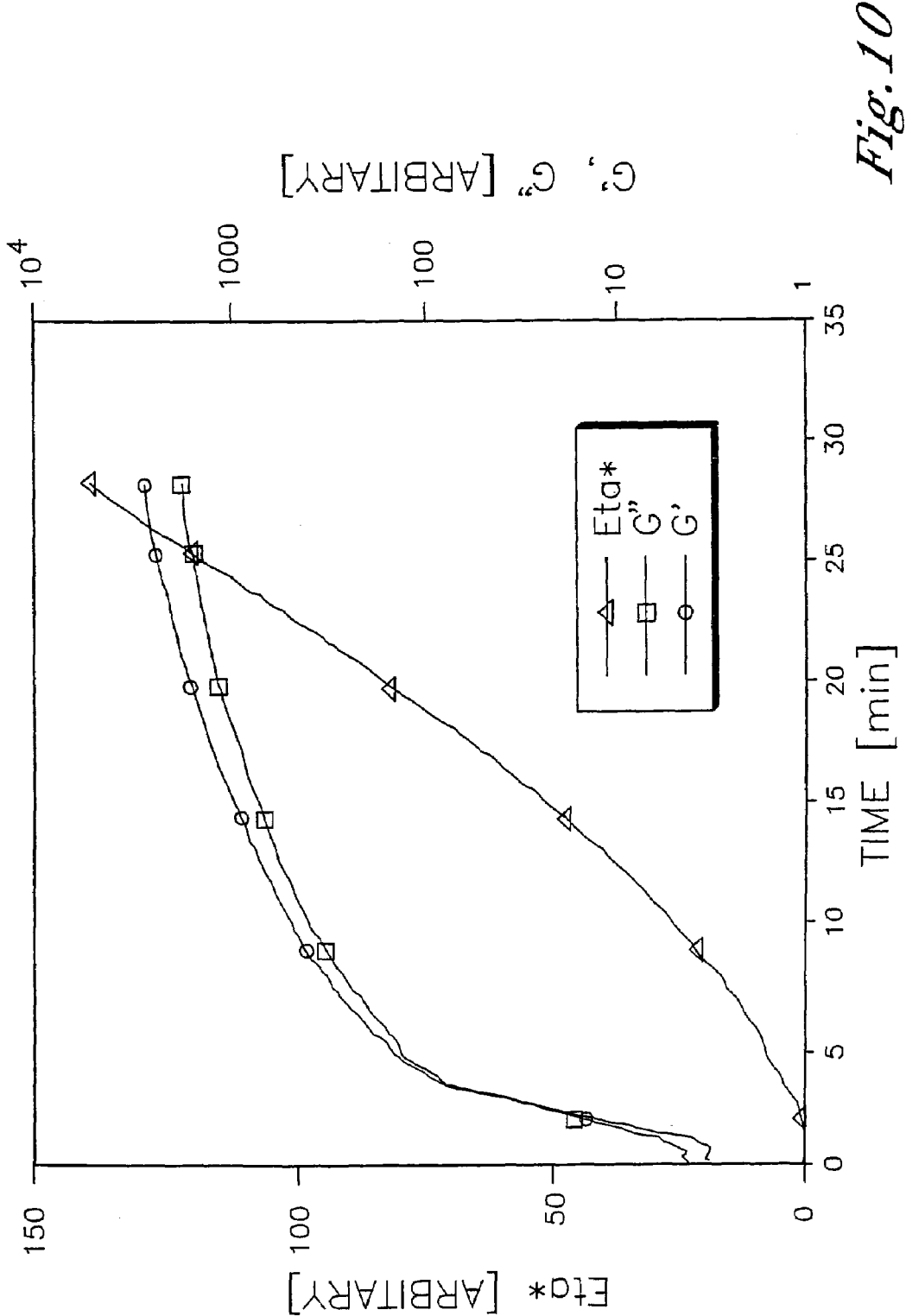
FIG. 10 provides a graphic representation of the viscoelastic properties of the composition disclosed in Example 6.

A 0.2 mm deep and 23 mm diameter circular trough was filled with 10 drops of a CAB refinish basecoat formulation using a 1-ml disposable Samco® transfer pipette (Samco Scientific Corporation, San Fernando, Calif.). The formulation contains polyester resin (78% total solution) in 3.9 percent, acrylic resin (40% total solution) in 21.8 percent, melamine in 0.7 percent, flow aid in 0.7 percent, silicone additive (10% total solution) in 0.3%, wax additive (5% total solution) in 7.3%, aluminum flake dispersion (35% total solution) in 9.1 percent, cellulose acetate butyrate (CAB 381 from Eastman Chemical Company, Kingsport, Tenn. in 10% total solution) in 32.5 percent and solvent blend in 23.7 percent. The solvent blend is composed of a 20/30/10/20/20 mixture of methyl isobutyl ketone, methyl amyl ketone, toluene, isobutyl alcohol, and acetone. The solution was spread evenly within the trough by using the edge of a glass slide. A T-bar probe with rectangular cross-section (0.15 mm×0.23×15 mm, height×width×length) was lowered to 0.05 mm gap. The dynamic test was conducted on a stress-controlled rheometer (AR 2000® from TA Instruments, New Castle, Del.) with 100% strain and 25 rad/sec frequency at ambient temperature. The complex viscosity and the moduli are plotted in FIG. 10.

We claim:

1. An apparatus for monitoring the viscoelastic properties of a liquid film comprising:
   (i) a substrate capable of supporting the liquid film,
   (ii) a T-bar probe with a diameter from about 0.01 mm to about 2 mm mounted so as to contact the liquid film,
   (iii) a means of effecting relative movement between the probe and the substrate so that the probe moves relative to the liquid film, and
   (iv) a means of monitoring the resistance to movement of the probe contacting the liquid,
   wherein the probe has sufficient surface area contacting the liquid film so that it may detect the resistance without interfering with the solidification of the liquid film.

2. An apparatus as recited in claim 1, wherein the substrate is a trough.

3. An apparatus as recited in claim 2, wherein the trough has a depth from about 0.005 mm to about 5 mm.

4. An apparatus as recited in claim 1, wherein the substrate is a flat plate.

5. An apparatus as recited in claim 1, wherein the means for monitoring the resistance of the movement of the probe is a transducer and the means for moving the substrate relative to the probe is a motor.

6. An apparatus as recited in claim 1, wherein the probe penetrates the liquid film and wherein the probe does not contact the substrate.

7. An apparatus as recited in claim 1, wherein the probe has a length from about 2 mm to about 50 mm.

8. An apparatus as recited in claim 1, wherein the probe has a length from about 5 mm to about 20 mm.

9. An apparatus as recited in claim 1, wherein the probe has a length from about 10 mm to about 15 mm.

10. An apparatus as recited in claim 1, wherein the probe has a diameter from about 0.025 mm to about 0.3 mm.

11. A process for monitoring the viscoelastic properties of a liquid film, wherein said liquid film is located on a substrate, wherein said process comprises the steps of:
    (i) contacting a T-bar probe with the liquid film;
    (ii) moving the probe relative to the substrate so that the probe moves with respect to the surface of the substrate and in contact with the liquid film while the liquid film is solidifying; and
    (iii) monitoring the change in the solidification properties of the liquid film,
    wherein the probe has sufficient surface area contacting the liquid film to detect the change in properties without interfering with the solidification of the liquid film.

12. A process as recited in claim 11, wherein the probe penetrates the liquid film.

13. A process as recited in claim 11, wherein the substrate is a trough.

14. A process as recited in claim 11, wherein the substrate is a flat plate.

15. A process as recited in claim 11, wherein the moving of the probe is in an oscillating motion.

16. A process as recited in claim 11, wherein the solidification properties monitored are the change in viscosity of the film and the change in the elasticity of the film over time.

17. A process as recited in claim 11, wherein the probe does not contact the substrate.

* * * * *